US008524771B2

(12) United States Patent
Malik

(10) Patent No.: US 8,524,771 B2
(45) Date of Patent: *Sep. 3, 2013

(54) WOUND AND SKIN CARE COMPOSITIONS

(75) Inventor: Sohail Malik, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,633

(22) Filed: Nov. 23, 2010

(65) Prior Publication Data

US 2011/0092522 A1 Apr. 21, 2011

Related U.S. Application Data

(63) Continuation of application No. 11/511,857, filed on Aug. 29, 2006, now Pat. No. 8,343,935, and a continuation of application No. 10/320,730, filed on Dec. 16, 2002, now Pat. No. 7,098,189.

(51) Int. Cl.
*A61K 31/215* (2006.01)

(52) U.S. Cl.
USPC .......................................................... 514/530

(58) Field of Classification Search
USPC .......................................................... 514/530
See application file for complete search history.

(56) References Cited

U.S. PATENT DOCUMENTS

| | | | |
|---|---|---|---|
| 4,518,614 A | 5/1985 | Parkinson | |
| 5,151,425 A | 9/1992 | Clark | |
| 5,487,899 A | 1/1996 | Davis | |
| 5,547,988 A | 8/1996 | Yu et al. | |
| 5,602,139 A | 2/1997 | Rattan | |
| 5,821,237 A * | 10/1998 | Bissett et al. | 514/75 |
| 5,863,544 A | 1/1999 | Willcox et al. | |
| 5,939,085 A | 8/1999 | Jacobs et al. | |
| 6,051,602 A * | 4/2000 | Bissett | 514/456 |
| 6,121,317 A | 9/2000 | Wu et al. | |
| 6,255,297 B1 | 7/2001 | Dalko et al. | |
| 6,333,180 B1 | 12/2001 | Farbood et al. | |
| 6,469,061 B1 | 10/2002 | Flescher et al. | |
| 7,258,878 B2 | 8/2007 | Greene et al. | |
| 7,365,097 B2 * | 4/2008 | Neuwels et al. | 514/530 |
| 7,485,666 B2 | 2/2009 | Villanueva et al. | |
| 7,608,642 B2 | 10/2009 | Malik et al. | |
| 2003/0206893 A1 | 11/2003 | Malik | |
| 2004/0029839 A1 | 2/2004 | Boulle et al. | |

FOREIGN PATENT DOCUMENTS

| | | |
|---|---|---|
| EP | 1333021 A2 | 8/2003 |
| WO | WO 9108751 | 6/1991 |
| WO | WO 9620703 | 7/1996 |
| WO | WO 02080890 A2 | 10/2002 |
| WO | WO03094907 A1 | 11/2003 |

OTHER PUBLICATIONS

Article—*Acne*, Braverman, The Journal of Investigative Dermatology, vol. 73, No. 5, Part II, 1979, pp. 434-442.
Article—*Age, sunlight, and facial skin: A histologic and quantitative study*, Warren et al, Journal of the American Academy of Dermatology, vol. 25, No. 5, Part I, Nov. 1991, pp. 751-760.

Article—*An Animal Model of Solar-Aged Skin: Histological, Physical, and Visible Changes in UV-Irradiated Hairless Mouse Skin*, Bissett et al., Photochemistry and Photobiology, vol. 46, No. 3, Sep. 1987, pp. 367-378.
Article—*Beauty Masks*, Morgan D. Gaffney, Cosmetics Science and Technology, $2^{nd}$ Ed., vol. 1, 1972, pp. 307-315.
Article—*Collagen Metabolism in Ultraviolet Irradiated Hairless Mouse Skin and Its Correlation to Histochemical Observations*, Kligman et al., The Journal of Investigative Dermatology, vol. 93, No. 2, Aug. 1989, pp. 210-214.
Article—*Connective Tissue Alterations in the Skin of Ultraviolet Irradiated Hairless Mice*, E. Schwartz, The Journal of Investigative Dermatology, vol. 91, No. 2, Aug. 1988, pp. 158-161.
Article—*The Contributions of UVA and UVB to Connective Tissue Damage in Hairless Mice*, Kligman et al., The Journal of Investigative Dermatology, vol. 84, No. 4, 1985, pp. 272-276.
Article—*Elastoderma—Disease of Elastin Accumulation within the Skin*, Kornberg et al., The New England Journal of Medicine (Medical Intelligence), vol. 312, No. 12, Mar. 21, 1985, pp. 771-774.
Article—*Hand Creams and Lotions*, S. J. Strianse, Cosmetics Science and Technology, $2^{nd}$ Ed., vol. 1, pp. 189-193, 1972.
Article—*Proposed Procedure of the Allocation of Trivial Names to the Gibberellins*, MacMillan et al., Nature, vol. 217, Jan. 13, 1968, pp. 170-171.
Article—*Permanent Waving*, Gershon et al., Cosmetics Science and Technology, $2^{nd}$ Ed., vol. 2, pp. 188-193, 1972.
Article—*Physiology of the Skin and its Appendages*, Waldman et al., Cosmetics Science and Technology, $2^{nd}$ Ed., vol. 3, pp. 188-193-, 1972.
Article—*Retinoic Acids Promote the Repair of the Dermal Damage and the Effacement of Wrinkles in the UVB-Irradiated Hairless Mouse*, Bryce et al., The Journal of Investigative Dermatology, vol. 91, No. 2, Aug. 1988, pp. 175-180.
Article—*Topical Tretinoin Improves Photoaged Skin—A Double-blind Vehicle-Controlled Study*, Weiss et al., The Journal of the American Medical Association, vol. 259, No. 4, Jan. 22/29, 1988, pp. 527-532.
Article—*Wrinkles due to idiopathic loss of mid-dermal elastic tissue*, Shelley et al., British Journal of Dermatology, vol. 97, Jul.-Dec. 1977, pp. 441-445.
Editorial—*The aging of skin: chronoaging versus photoaging*, A. Oikarinen, Photodermatology, Photoimmunology & Photomedicine, vol. 7, 1990, pp. 3-4.
Product Information from CTFA International Cosmetic Ingredient Dictionary, $4^{th}$ Ed., 1991, pp. 12 and 80.
Product Information from The Merck Index, An Encyclopedia of Chemicals, Drugs, and Biologicals, $10^{th}$ Ed., Windholz (Editor), 1983, p. 463 for 3167. *Dihydroxyacetone*.
Request for Ex Parte Reexamination Transmittal Form (2 pages) and Ex Parte Reexamination Request for U.S. Patent No. 7,098,189 (41 pages), dated Jun. 9, 2010.
Order Granting/Denying Request for Ex Parte Reexamination dated Jun. 23, 2010, 13 pages.
French Application along with English Translation with Certification(U.S. Appl. No. 60/357,620), Feb. 20, 2002, 50 pages.

* cited by examiner

*Primary Examiner* — Elli Peselev
(74) *Attorney, Agent, or Firm* — Dority & Manning, P.A.

(57) ABSTRACT

The invention provides compositions and methods that employ compounds that can stimulate proliferation of fibroblasts or keratinocytes and/or stimulate production of collagen by fibroblasts. These compositions and methods are useful for treating gum- and skin-related conditions.

17 Claims, 3 Drawing Sheets

WOUND AND SKIN CARE COMPOSITIONS

RELATED APPLICATIONS

The present application is a continuation of U.S. application Ser. No. 11/511,857 (now U.S. Pat. No. 8,343,935), which was filed on Aug. 29, 2006, and is a continuation of U.S. application Ser. No. 10/320,730, which was filed on Dec. 16, 2002 (now U.S. Pat. No. 7,098,189). The contents of both applications are incorporated herein in their entirety by reference thereto for all purposes. All statements, arguments, or positions taken by Applicant during prosecution of the '857 application, '730 application, or during the reexamination of the '189 patent, are hereby expressly rescinded.

FIELD OF THE INVENTION

The present invention relates generally to the field of wound healing and to the repair and maintenance of healthy skin.

BACKGROUND OF THE INVENTION

Skin is subject to insults by many extrinsic and intrinsic factors. Extrinsic factors that can adversely affect the skin include ultraviolet radiation (e.g., from sun exposure), environmental pollution, wind, heat, low humidity, harsh surfactants, abrasives, and the like. Intrinsic factors that lead to skin problems include chronological aging and other biochemical changes from within the skin. Whether extrinsic or intrinsic, these factors result in visible signs of skin aging and damage, such as wrinkling, roughness and histological changes. Moreover, to many people, skin wrinkles are a reminder of the disappearance of youth. As a result, the elimination of wrinkles has become a concern for many people. Anti-wrinkle treatments range from cosmetic creams and moisturizers to various forms of cosmetic surgery.

Extrinsic or intrinsic factors may result in the thinning and general degradation of the skin. For example, as the skin naturally ages, there is a reduction in the cells and the blood vessels that supply the skin. There is also a flattening of the dermal-epidermal junction that results in weaker mechanical resistance of this junction. See, for example, Oikarinen, "The Aging of Skin: Chronoaging Versus Photoaging," Photodermatol. Photoimmunol. Photomed., vol. 7, pp. 3-4, 1990, which is incorporated by reference herein in its entirety.

Skin contains an elaborate network of elastin fibers that is responsible for maintaining its elastic properties. With excessive exposure to sunlight the elastic fiber system becomes hyperplastic, disorganized and ultimately disrupted. This process is known as actinic elastosis and it is a principal cause of wrinkling, discoloration and laxity of the skin in the exposed areas of the body. As new fibroblasts, endothelial cells and keratinocytes form, the skin can repair itself. However, the skin becomes less able to do so as it ages. Therefore, agents that can accelerate the growth and repair of prematurely aged skin are needed.

Wound healing is also accelerated by increased cellular proliferation and migration of certain cell types. The mechanisms involved in wound healing are often divided into four phases: hemostasis, inflammation, proliferation and maturation. During inflammation, leucocytes accumulate to combat bacteria and the permeability blood vessel walls increases, leading to swelling. If an infection does not develop the number of leucocytes diminishes. Monocytes replace the leukocytes. Macrophages and lymphocytes release growth factors (cytokines) as well as a number of chemical substances, such as histamine, serotonin, and prostaglandins. These substances help regulate the wound healing process. In the proliferation phase, new fibroblasts, endothelial cells and keratinocytes arise, connective tissue is formed, new blood vessels grow and injured tissue is regenerated. Fibroblasts become dominant after about a week, the inflammation decreases and the strength of the tissues around the wound site increases rapidly. During the maturation phase collagen is laid down and scar tissue is formed. This maturation phase might go on for a long time during which time, tissues of various types are regenerated. In order to obtain an optimal healing of skin and associated tissues, the supply of different vitamins and trace elements as well as nutrients should be sufficient as well as the oxygen supply.

While certain skin care compositions are available on the market, such compositions do not effectively stimulate the growth of new skin tissues. Hence, there is a need for formulations that not only improve the appearance but also the health of skin. Ideally, such formulations would provide a range of useful activities such as, for example, wound healing, scar reduction, soothing rashes, eliminating wrinkles and reducing the signs of aging.

SUMMARY OF THE INVENTION

The invention provides compositions that can stimulate the formation of new skin and gum tissues, facilitate wound healing, and ameliorate the effects of aging. In particular, the compositions and methods of the invention can stimulate cellular proliferation of mammalian fibroblasts or keratinocytes. Not only can these compositions stimulate cell growth and the repair of skin and gum tissues, but they can also stimulate collagen production in mammalian fibroblasts.

Thus, the invention provides compositions comprising a dermatologically or pharmaceutically acceptable carrier and an effective amount of a jasmonic acid compound, a gibberellic acid compound or a zeatin compound; wherein the composition can stimulate cellular proliferation of mammalian fibroblasts or keratinocytes. Such compositions are useful for treating wounds, stimulating gum tissue growth and for reversing the effects of aging on skin.

In other embodiments, the invention provides a composition comprising a dermatologically or pharmaceutically acceptable carrier and an effective amount of a jasmonic acid compound, a gibberellic acid compound or a zeatin compound; wherein the composition can stimulate collagen production in mammalian fibroblasts. Such compositions are useful for treating wounds, stimulating gum tissue growth and for reversing the effects of aging on skin.

Further embodiments of the invention relate to compositions comprise a dermatologically or pharmaceutically acceptable carrier and an effective amount of a hydroxy acid compound, wherein the composition can stimulate cellular proliferation of mammalian fibroblasts or keratinocytes. Such compositions can further comprise an effective amount of a jasmonic acid compound, a gibberellic acid compound or a zeatin compound.

The present invention also provides an orally acceptable formulation for the treatment of gum tissues comprising an acceptable carrier and an effective amount of a jasmonic acid compound, a gibberellic acid compound or a zeatin compound; wherein the formulation can stimulate cellular proliferation of mammalian fibroblasts or keratinocytes. The composition can stimulate collagen production in mammalian fibroblasts.

In one embodiment, the invention provides a composition comprising:
a) from about 0.01% to about 30%, by weight of the composition, of jasmonic acid, gibberellic acid or zeatin;
b) from about 0.01% to about 30%, by weight of the composition, of acetylsalicylic acid or salicylic acid; and
c) a dermatologically or pharmaceutically acceptable carrier.

The invention also provides a method of stimulating growth of fibroblasts or keratinocytes comprising administering to the fibroblasts or the keratinocytes a safe and effective amount of a composition comprising a dermatologically acceptable carrier and an effective amount of a hydroxy acid compound, wherein the composition can stimulate cellular proliferation of mammalian fibroblasts or keratinocytes.

In another embodiment, the invention provides a method of stimulating growth of fibroblasts or keratinocytes comprising administering to the fibroblasts or the keratinocytes a safe and effective amount of a composition comprising a dermatologically acceptable carrier and an effective amount of a jasmonic acid compound, a gibberellic acid compound or a zeatin compound; wherein the composition can stimulate cellular proliferation of mammalian fibroblasts or keratinocytes.

The invention also provides a method of stimulating collagen production in mammalian fibroblasts comprising administering to the fibroblasts a safe and effective amount of a composition comprising a dermatologically acceptable carrier and an effective amount of a jasmonic acid compound, a gibberellic acid compound or a zeatin compound; wherein the composition can stimulate collagen production in mammalian fibroblasts. The composition can further comprise a hydroxy acid compound.

In some embodiments, the effective amount of the jasmonic acid compound, the gibberellic acid compound or the zeatin compound is a concentration of about 0.001 micromolar to about 10 millimolar. In other embodiments, the effective amount of the jasmonic acid compound, the gibberellic acid compound or the zeatin compound is a concentration of about 1 micromolar to about 5 millimolar.

The compositions can have one or more additional ingredients. For example, the compositions can have additional ingredients such as desquamation compounds, anti-acne compounds, anti-wrinkle compounds, vitamin $B_3$ compounds, vitamin E compounds, retinoid compounds, hydroxy acid compounds, anti-oxidant compounds, radical scavengers, chelating agents, flavonoid compounds, anti-inflammatory agents, anti-cellulite agents, topical anesthetics, tanning compounds, skin lightening agents, skin healing compounds, anti-microbial compounds, antifungal compounds, sunscreen compounds, particulate material, moisturizers, or thickening agents.

Examples of vitamin E compounds that can be used include tocopherol, tocopherol acetate, a tocopherol ester or a mixture thereof. Examples of retinoid compounds that can be used include retinal, retinal, retinol ester, retinyl propionate, retinoic acid, retinyl palmitate, or a mixture thereof. Particulate materials that may be employed include mica, mica treated with barium sulfate and $TiO_2$, silica, nylon, polyethylene, talc, styrene, polypropylene, ethylene/acrylic acid copolymer, sericite, aluminum oxide, silicone resin, barium sulfate, titanium dioxide, iron oxide, bismuth oxychloride, calcium carbonate, cellulose acetate, polymethyl methacrylate, or a mixture thereof. Sunscreens that can be used include, for example, a metallic oxide selected from the group consisting of titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, or a mixture thereof. Other sunscreens that may be used include octylmethoxycinnamate, octyl salicylate, terephthalyidene dicamphor sulfonic acid, avobenzone, octocrylene, or a mixture thereof.

DETAILED DESCRIPTION OF THE INVENTION

Figure 1:
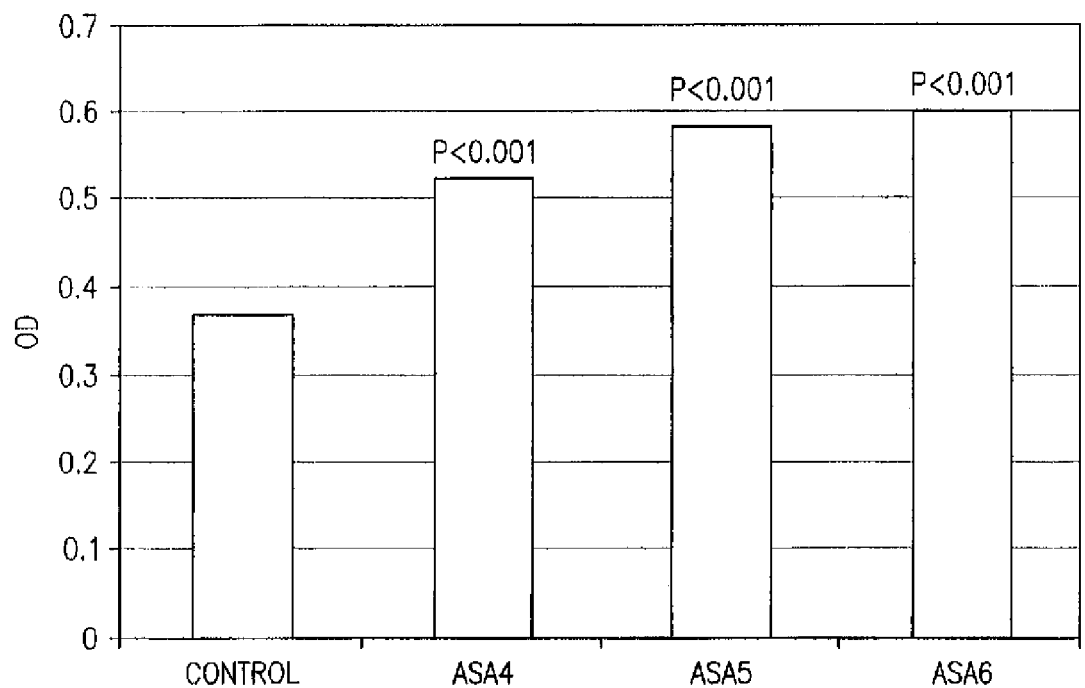
FIG. 1 illustrates the cell proliferating activity of acetylsalicylic acid on human skin fibroblasts. The optical density (OD) at 490 nm was used as a measure of cellular density. The concentration of acetylsalicylic acid tested varied between $1 \times 10^{-4}$ M (designated ASA4), $1 \times 10^{-5}$ M (designated ASA5) and $1 \times 10^{-6}$ M (designated ASA6). Control cells received no acetylsalicylic acid. As illustrated, all concentrations of acetylsalicylic acid had a significant effect on cell growth ($P<0.001$). However, the effect of acetylsalicylic acid was dose dependent, with a greater effect observed at lower concentrations.

The invention provides compositions for increasing cell proliferation and for stimulating collagen production in keratinous tissues such as the skin. These compositions can be used to reverse the effects of aging. Such compositions are useful for treating wounds, stimulating gum tissue growth and for reversing the effects of aging on skin. Such compositions are useful for treating wounds, stimulating gum tissue growth and for reversing the effects of aging on skin. Such compositions are useful for treating wounds, stimulating gum tissue growth and for reversing the effects of aging on skin. Such compositions are useful for treating wounds, stimulating gum tissue growth and for reversing the effects of aging on skin. The compositions of the invention can contain an effective amount of a hydroxy acid compound, a jasmonic acid compound, a gibberellic acid compound or a zeatin compound as well as acceptable carriers and other ingredients.

Definitions

The term "keratinous tissue," as used herein, refers to keratin-containing layers disposed as the outermost protective covering of mammals (e.g., humans, dogs, cats, etc.) that includes, but is not limited to, skin, lips, hair, toenails, fingernails, cuticles, hooves, etc.

The term "topical application", as used herein, means to apply or spread the compositions of the present invention onto the surface of the keratinous tissue.

The term "dermatologically-acceptable," as used herein, means that the described compositions or components thereof are suitable for use in contact with mammalian keratinous tissue without undue toxicity, incompatibility, instability, allergic response, and the like.

The term "safe and effective amount" as used herein means an amount of a compound or composition sufficient to significantly induce a positive benefit, such as a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The term "sagging" as used herein means the laxity, slackness, or the like condition of skin that occurs as a result of loss of, damage to, alterations to, and/or abnormalities in dermal elastin.

The terms "smoothing" and "softening" as used herein mean altering the surface of the keratinous tissue such that its tactile feel is improved.

"Signs of skin aging" include, but are not limited to, all outwardly visible or tactilely perceptible manifestations as well as any other macro or micro effects due to skin aging. Such signs may be induced or caused by intrinsic factors or extrinsic factors, e.g., chronological aging and/or environmental damage. These signs may result from processes that include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

Effects of Aging on Skin

Skin, which is the external covering of the body, has two components: the epidermis that contains four layers and the dermis, also referred to as the corium, cutis, derma, or true skin, that contains a superficial papillary layer and a deep reticular layer. Collagen constitutes about 80% of the dry weight of the dermis and is the major fibrillar component of human skin. The dermis is composed of connective tissue that contains lymphatics, nerves and nerve endings, blood vessels, sebaceous and sweat glands, and elastic fibers that provide the elastic properties of the skin. The mature fiber contains about 90% elastin and two glycosaminoglycans are present at concentrations of about 2% and 0.1%, respectively (see, e.g., Braverman (1982) J. Invest. Dermatol, 78:434-443). The coarse branching fibers are entwined with collagen fiber bundles in the reticular dermis. The fibers rise from the deeper layers of the papillary layer of the dermis and, as they rise towards the epidermis, they split repeatedly become finer and form a network.

As humans age, there are changes in the quantity and integrity of dermal elastic tissue (Warren et al. (1991) J. of the American Acad. Dermatology 25:751-760). Gross alteration in elastin leads to alterations in the appearance of the skin (see, Bryce et al. (1988) J. Invest. Dermatology 91:175-180; Kornberg et al. (1985) New Engl. J. Med, 312:771-774; Shelley et al. (1977) Br. J. Dermatol, 7:441-445). The association of changes in the fibers and the appearance of wrinkles indicate a causal relationship between the integrity of the elastic fiber network and the mechanical properties of the skin. Aging skin is characterized by initial elastogenesis followed by a slow spontaneous progressive degradation of the elastic fibers that leads to laxity and wrinkling. Studies of skin from subjects of various ages indicate that the degradation of elastic fibers that begins about age 30 and becomes marked after age 70 is a major feature of aging skin.

In understanding the process of aging of human skin, it is pertinent to understand the role of fibroblasts, particularly in the dermis of human skin and in the corresponding connective tissue layer underlying the integuments of other mammals and the epithelia of the inner wall of the gastrointestinal tracts of humans and other animals. Fibroblasts synthesize components that are required for maintenance of the structural, functional and cosmetic integrity of the skin and the structural and functional integrity of other surface tissues covered by epithelia. These components include collagen and elastin, which are fibrous proteins responsible for the three-dimensional architecture of skin and the other surface tissues, fibronectin, which is a protein responsible for cell anchorage and maintenance of cell morphology; and a number of proteinaceous growth factors essential for the maintenance of epithelia and basal cell layers and connective tissue layers underlying them. Available evidence indicates that protein biosynthetic activity of fibroblasts decreases significantly with age. For example, the rate of collagen synthesis at about 70% of life expectancy for human fibroblasts in culture is only about 50% of that of such fibroblasts at less than 20% of life expectancy.

The changes in the appearance of the skin with age result from natural or intrinsic aging superimposed by actinic damage resulting from photoaging (see, e.g., Weiss et el. (1988) J. American Medical Assoc. 259:527-532). Intrinsic aging includes changes that occur as a result of endogenous factors and genetically programmed senescence, including epidermal and dermal atrophy. Photoaging results from long-term exposure to UV (ultra-violet) radiation, primarily from the sun. Ultraviolet exposure is also associated with tumor induction and other skin pathologies. Ultraviolet radiation from the sun includes UVB (280-315 nm) and the more penetrating UVA (315-400 nm) radiation. UVB causes erythema, skin cancer and dermal connective tissue damage. UVA also causes erythema and is carcinogenic at higher doses. Low doses (2.5 minimal erythemic doses (MEDs)) are sufficient to cause endothelial cell enlargement, extravasation of blood cells, and perivenular neutrophil infiltrates as wells increased concentrations of mediators of the inflammatory response (see, e.g., Kligman et al. (1985) J. Invest. Dermatol. 84:272-276).

Long-term ultraviolet exposure results in histological and visible changes in the skin, including: damage to the underlying connective tissue, manifested as elastosis and increases in the glycosaminoglycans and loss of collagen; dermal accumulation of elastin-staining material resulting from the degenerative changes in collagen fibers; epidermal dysplasia with cytologic atypia and loss of polarity of keratinocytes; and an inflammatory infiltrate (see, e.g., Bissett et al. (1987) Photochemistry and Microbiology 46:367-378). The degradation of elastic fibers and wrinkling associated with intrinsically aging skin also accompanies photoaging. In humans, advanced photodamage can be detected in the staining properties of dermal tissue resulting from changes in the insoluble and soluble fractions of collagen that occur as the entire upper dermis becomes filled with elastosis (Kligman et al. (1989) J. Investigative Dermatol. 93:210-214). The changes in collagen and elastic fiber over decades of such exposure result in skin that is wrinkled, yellowed, blotchy, lax, rough and leathery. Scanning electron microscopy of aged skin indicates that the network of elastic fibers becomes denser and has a more disorganized arrangement than younger skin.

Exposure to sunlight is such a pronounced factor in premature aging that by middle age individuals who have been exposed to more sunlight appear older than those who have not. The extent of dermal degenerative change correlates with the visible signs of premature aging. The subepidermal band of normal dermis, which is a site of continual dermal repair, contains normal collagen fibers. This zone becomes visually evident, however, only after there is sufficient elastotic damage to delineate this region. The elastotic material is composed principally of elastin and microfibrillar proteins that codistribute with fibronectin (see, Schwartz (1988) J. Invest. Dermatol. 1:158-161). Actinic elastosis appears to be reversible to some extent by treatment with chemical peels, dermabrasion or topical application of tretinoin (see, e.g., Warren et al. (1991) J. American Acad. Dermatol. 25:751-760; and Weiss et al. (1988) J. American Medical Assoc. 259:527-532).

Hydroxy Acids

The compositions of the present invention may contain a safe and effective amount of a hydroxy acid. The hydroxy acids can be alpha-hydroxy or beta-hydroxy acids. Examples of hydroxy acids for use in the compositions of the present invention include salicylic acid, lactic acid, glycolic acid, acetylsalicylic acid, and other salicylic acid derivatives. In some embodiments, salicylic acid and the synthetic and naturally occurring derivatives of salicylic acid can be used in the compositions and methods of the present invention.

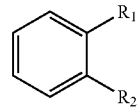

wherein:
R1 is COOR, or —(CH$_2$)n-OX
R is H, or alkyl (e.g., with one to twenty carbons);
n is an integer of about 1 to about 20;
X is H, or 1 to 6 sugar residues (e.g., hexoses or pentoses);
R2 is COOR, —(CH$_2$)n-OX, OCO-alkyl (C1-C20), OY;
and
Y is H, alkyl (C1-20), or 1 to 6 sugar residues (e.g., hexoses or pentoses).

In general, the alkyl groups employed in these hydroxy acid compounds have about one to twenty carbon atoms, although in some embodiments lower alkyl groups are used, for example, alkyl groups with about one to eight carbon atoms. Alkyl groups with even lower numbers of carbon atoms can also be used, for example, alkyl groups with one to six, or one to three carbon atoms.

In some embodiments, salicylic acid is employed in the compositions of the invention. Salicylic acid is a compound of formula I wherein R1 is COOH and R2 is OH. In other embodiments, acetylsalicylic acid is employed in the compositions of the invention. Acetylsalicylic acid is a compound of formula I wherein R1 is COOH and R2 is OCOCH$_3$.

When present in the compositions of the present invention, salicylic acid or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of acetylsalicylic acid or salicylic acid that range from about $10^{-4}$ M to about $10^{-6}$ M are effective for increasing cell proliferation and stimulating the production of collagen in mammalian keratinous tissue.

Gibberellic Acid

Gibberellic acid comprises a class of compounds that is also referred to as gibberellins. Gibberellins are plant hormones that affect a wide variety of processes throughout the life cycle of plants, including seed germination, stem elongation, flower induction, anther development, and seed and pericarp growth. Gibberellins are tetracyclic diterpenoid acids found in fungi and higher plants having the ent-gibberellane ring system shown in the following structure (II).

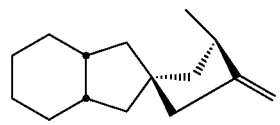

Gibberellins were first isolated by Japanese researchers in the 1930s from cultures of the fungus *Gibberella fujikuroi* (*Fusarium moniliforme*). These secondary metabolites have been shown to be present in other fungal species, in some ferns, and in many gymnosperms and angiosperms. Of the 121 known gibberellins, 96 have been identified only in higher plants, 12 are present only in *Gibberella*, and 12 are present in both. As in *Gibberella*, many different gibberellins can be present in individual angiosperms.

Two main types of gibberellins exist: the C20-gibberellins, which have 20 carbon atoms (structure III, below), and the C19-gibberellins, in which the twentieth carbon atom has been lost due to metabolism (structure IV, below). The carboxylic acid at carbon-19 bonds to carbon-10 to produce a lactone bridge in almost all of the $C_{19}$-gibberellins.

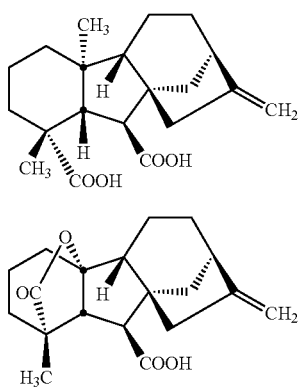

The ent-gibberellane ring system can contain many structural modifications, accounting for the large number of known gibberellins. Naturally occurring gibberellins with identified structures are allocated an "A number" (MacMillan et al. (1968) Nature 217:170-171). At present, 126 naturally occurring gibberellins of plant and fungal origin are known. Current structural information on gibberellins can be found at the website plant-hormones.bbsrc.ac.uk/gibberellin_information2.htm.

Variations in gibberellin structure arise in several ways. Carbon-20 can exist in different oxidative states, e.g., methyl (—$CH_3$), hydroxymethyl (—$CH_2OH$), aldehyde (—CHO), or carboxylic acid (—COOH). The ent-gibberellane skeleton, especially that of the C19-gibberellins, can also contain additional functional groups. Hydroxyl (—OH) groups are frequently inserted into the ring system; insertion of epoxide (>O) and ketone (=O) functions also occurs, although less commonly. The position and/or stereochemistry of substituent groups can affect the biochemical and physiological significance of the molecules. Substituent groups positioned above the ring plane are said to be in the β-configuration; their bonding to the ring is designated by a solid, elongated triangle.

Substituent groups positioned below the ring plane are said to be in the α-configuration; their bonding to the ring is designated by a dashed, elongated triangle. The attachment of substituent groups in the plane of the ring system is indicated by a straight line.

Gibberellins can exist as conjugates, for example with a molecule of glucose, either by an ether or an ester linkage. Such conjugation may temporarily or permanently inactivate a gibberellin.

The biological activity of different gibberellins varies, and various gibberellins within a plant can be precursors, biosynthetic intermediates, or deactivation products of active gibberellins. Three structural features are commonly associated with gibberellin biological activity: a 3-hydroxyl group, a 7-carboxyl group, and a lactone ring. Broadly speaking, a compound possessing the ent-gibberellane ring system but lacking one or more of these structural features can be considered a gibberellin precursor, an intermediate, or a derivative.

The compositions and methods of the invention generally employ active forms of gibberellic acids, for example, those having structures related to the following structure (V).

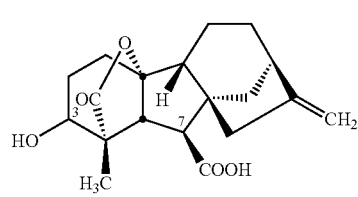

When present in the compositions of the present invention, gibberellic acids or their derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of an active gibberellic acid ranging from about $10^{-4}$ M to about $10^{-6}$ M are effective for increasing cell proliferation and stimulating the production of collagen in mammalian keratinous tissue.

Jasmonic Acid Compounds

Jasmonic acid compounds employed in the invention include jasmonic acid and jasmonic acid derivatives available to one of skill in the art. Such compounds include jasmonic acid, methyl jasmonate and their isomers. In the present invention jasmonic acid and jasmonic acid derivatives used also include synthetic and natural stereoisomers of jasmonic acid, dihydrojasmonic acid, hydroxy jasmonic acid and dihydro-hydroxy jasmonic acid. Further examples of jasmonic acid derivatives that may be used in the invention include compounds having any one of formulae VI.

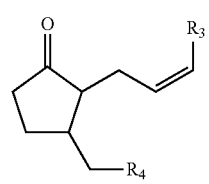

wherein:
R3 is alkyl;
R4 is COOR, or —($CH_2$)n-OX, where n is an integer of from 1 to 20;
R is H, or alkyl; and
X is H, or 1 to 6 sugar residues (e.g., hexose or pentose).

In general, the alkyl groups employed in these jasmonic acid compounds have about one to twenty carbon atoms, although in some embodiments lower alkyl groups are used, for example, alkyl groups with about one to eight carbon atoms. Alkyl groups with even lower numbers of carbon atoms can also be used, for example, alkyl groups with one to six, or one to three carbon atoms, In some embodiments, jasmonic acid is employed in the compositions of the invention. Jasmonic acid is a compound of formula VI wherein R3 is $C_2H_5$ and R4 is COOH.

Another jasmonic acid compound employed in the invention is a compound of formula VII.

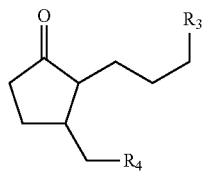

VII wherein:
R3 is alkyl;
R4 is COOR, or —(CH$_2$)n-OX, where n is an integer of from 1 to 20;
R is H, or alkyl; and
X is H, or 1 to 6 sugar residues (e.g., hexoses or pentoses).

In some embodiments, dihydrojasmonic acid is employed in the compositions of the invention. Dihydrojasmonic acid is a compound of formula VII wherein R3 is C$_2$H$_5$ and R4 is COOH.

Another jasmonic acid compound employed in the invention is a compound of formula VIII.

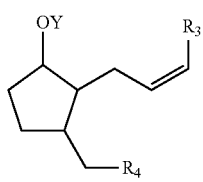

VIII wherein:
R3 is alkyl;
R4 is COOR, or —(CH$_2$)n-OX, where n is an integer of from 1 to 20;
R is H, or alkyl;
X is H, or 1 to 6 sugar residues (e.g., hexoses or pentoses); and
Y is H, alkyl, or 1 to 6 sugar residues (e.g., hexoses or pentoses).

In some embodiments, hydroxyjasmonic acid is employed in the compositions of the invention. Hydroxyjasmonic acid is a compound of formula VIII wherein R3 is C$_2$H$_5$ and R4 is COOH.

Another jasmonic acid compound employed in the invention is a compound of formula IX.

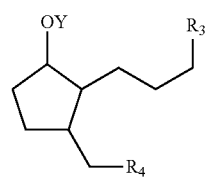

IX wherein:
R3 is alkyl;
R4 is COOR, or —(CH$_2$)n-OX, where n is an integer of from 1 to 20;
R is H, or alkyl;
X is H, or 1 to 6 sugar residues (e.g., hexoses or pentoses); and
Y is H, alkyl, or 1 to 6 sugar residues (e.g., hexoses or pentoses).

In some embodiments, dihydro-hydroxyjasmonic acid is employed in the compositions of the invention. Dihydro-hydroxyjasmonic acid is a compound of formula IX wherein R3 is C$_2$H$_5$ and R4 is COOH.

When present in the compositions of the present invention, jasmonic acids or jasmonic acid derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of jasmonic acid ranging from about $10^{-4}$ M to about $10^{-6}$ M are effective for increasing cell proliferation and stimulating the production of collagen in mammalian keratinous tissue.

Zeatin Compounds

Zeatin compounds employed in the invention include the cis and trans isomers of zeatin and the cis and trans isomers of zeatin derivatives available to one of skill in the art. Such zeatin compounds and zeatin derivatives can be natural and synthetic derivatives of the compounds provided by formula X below.

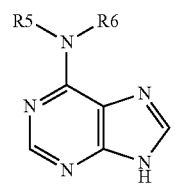

X wherein:
R5 is H, 3-hydroxymethyl-3-methylallyl, alkyl, —(CH$_2$)n-CH$_3$, or OZ;
Z is H, 1 to 6 sugar residues (e.g., hexoses or pentoses), or —(CH$_2$)n-furan;
R6 is H, 3-hydroxymethyl-3-methylallyl, alkyl, —(CH$_2$)n-C$_3$, or OZ; and
n is an integer of from about 1 to about 20.

In some embodiments, zeatin is employed in the compositions of the invention. Zeatin is a compound of formula X wherein R5 is 3-hydroxymethyl-3-methylallyl, and R6 is H.

When present in the compositions of the present invention, zeatin or its derivatives can be used in an amount of from about 0.001% to about 50%, or from about 0.01% to about 20%, or from about 0.01% to about 10%, or from about 0.05% to about 5%, or from about 0.05% to about 2% of the composition. According to the invention, in situ concentrations of zeatin ranging from about $10^{-4}$ M to about $10^{-6}$ M are effective for increasing cell proliferation and stimulating the production of collagen in mammalian keratinous tissue.

Effects of the Compositions on Keratinous Tissues

The compositions and methods of the invention are useful for stimulating cellular proliferation and/or collagen production in cells within keratinous tissues. Such proliferation and collagen production can therapeutically improve visible and/or tactile discontinuities in mammalian skin, including discontinuities in skin texture and color. For example, after exposure to the compositions of the invention, the apparent diameter of pores can decrease, the apparent height of tissue immediately proximate to pore openings approaches that of the interadnexal skin, the skin tone/color becomes more uniform, and/or the length, depth, and/or other dimension of lines or wrinkles are decreased.

The compositions of the present invention are also useful for regulating the condition of skin and especially for regulating keratinous tissue condition. Regulation of skin condition, namely mammalian and in particular human skin condition, is often required due to conditions that may be induced or caused by factors internal and/or external to the body. Examples include, environmental damage, radiation exposure (including ultraviolet radiation), chronological aging, menopausal status (e.g., post-menopausal changes in skin), stress, diseases, etc. For instance, "regulating skin condition" includes prophylactically regulating and/or therapeutically regulating skin condition, and may involve one or more of the following benefits: thickening of skin (i.e., building the epidermis, dermis, sub-dermal, subcutaneous fat, or underlying muscle layers of the skin) and, where applicable the keratinous layers of the nail and hair shaft, to reduce skin atrophy. The compositions and methods of the invention can also increase the convolution of the dermal-epidermal border (also known as the rete ridges), prevent loss of skin elasticity resulting from loss, damage and/or inactivation of functional skin elastin, prevent such as elastosis, sagging, loss of skin recoil from deformation; non-melanin skin discoloration such as under eye circles, blotching (e.g., uneven red coloration due to, e.g., rosacea) (hereinafter referred to as "red blotchiness"), sallowness (pale color), discoloration caused by telangiectasia or spider vessels.

As used herein, prophylactically regulating skin condition includes delaying, minimizing and/or preventing visible and/or tactile discontinuities in skin (e.g., texture irregularities in the skin which may be detected visually or by feel).

As used herein, therapeutically regulating skin condition includes ameliorating, e.g., diminishing, minimizing and/or effacing, discontinuities in skin.

Dental Applications

The invention also contemplates compositions for stimulating cellular proliferation of gum tissues. Such compositions and formulations are useful for treating or preventing a variety of dental and oral conditions, including gum recession, gingivitis and gum disease. These compositions can contain an effective amount of a hydroxy acid compound, a jasmonic acid compound, a gibberellic acid compound or a zeatin compound as well as an orally acceptable carrier and other ingredients. Such compositions can be formulated as mouthwashes, as a gel for use in a dental tray that can cup the teeth or as a adhesive that can stick to tooth or gum surfaces.

In some embodiments, the carrier will include a tackifying agent and a solvent, which together yield a sticky matrix material. The matrix material can be sufficiently sticky to enable a dental tray to be held and retained against a person's teeth. Suitable sticky matrix materials are preferably viscous and do not readily dissolve in saliva. Various tackifying agents are available and the selection of the tackifying agent can readily be made by one of skill in the art. One tackifying agent that can be used to form a sticky and viscous matrix material comprises carboxypolymethylene, for example, CARBOPOL 934P. Carboxypolymethylene can be used to form a glue-like dental composition that itself can act as an adhesive in holding a comfortable, non-self-retaining dental tray against a person's teeth. The use of carboxypolymethylene eliminates the need to use dental trays that are self-retaining (i e., typically trays that are rigid and which mechanically interlock over a person's teeth or gums and which are intended for use with less sticky compositions). See U.S. Pat. No. 6,309,625.

In general, the dental compositions of the present invention can include carboxy-polymethylene in a concentration in a range from about 0.5% to about 25% by weight of the dental composition, or in a range from about 2% to about 12% and or in a range from about 3% to about 10%. Where is it desired to increase the stickiness, viscosity and resistance to dilution to saliva, one may adjust the concentration of carboxypolymethylene to achieve a desired level of any or all of these properties. Increased stickiness assists in retaining the preferred dental trays against a person's teeth. Alternatively, compositions can be made less adhesive and tacky if desired, particularly is applied directly without a dental tray.

In order to obtain good dispersion of the carboxypolymethylene resin within the dental composition, it is recommended that the carboxypolymethylene be mixed with a suitable solvent before attempting to add other components that are less compatible with carboxypolymethylene, such as water. Examples of suitable solvents for use with carboxypolymethylene include glycerin, other polyhydric alcohols, polyalkylene glycols and other polyols, and the like. Glycerin appears to enable larger quantities of carboxypolymethylene to be dispersed in water. It is preferable that the concentration of glycerin, polyol, or like substance utilized as a solvent in the dental whitening compositions be added in a range from about 15% to about 85% by weight of the dental whitening compositions, more preferably in a range from about 25% to about 75% by weight, and most preferably in a range from about 30% to about 65% by weight. It should be understood, however, that the actual amount of carboxypolymethylene is not critical for obtaining a sticky, viscous dental composition.

The sticky matrix material may include other tackifying components that in combination with, or in lieu of some or all of, the carboxypolymethylene will yield a gum stimulating composition having the desired level of stickiness needed to hold a preferred, comfortable-fitting dental tray in place over a person's teeth. Other synthetic polymers and/or natural gums, proteins, or other gel-forming admixtures can be used so long as they yield a sticky gum stimulating composition.

In addition to earboxypolymethylene, examples of other suitable tackifying and thickening agents include gums such as xanthan gum, talha gum, tragacanth gum, locust bean gum, guar gum, Irish moss gum, ghatti gum, furcelleran gum, carrageenan gum, arabic gum, alginic acid gum, agar gum, alginate gum. Another suitable tackifying agent is sold as PEMULEN™, a proprietary compound from B.F. Goodrich, or a compositional or chemical equivalent thereof. PEMULEN™ includes a significant quantity of a polyacrylic copolymer that has a slightly hydrophobic end and a strongly hydrophilic end. Additional examples of suitable tackifying agents include polyethylene oxides such as POLYOX™ sold by Union Carbide. These tackifying agents may be present in the same ranges as discussed above in relation to carboxypolymethylene One of skill in the art may include other active dental agents to treat or prevent other types of dental and/or gum problems. For example, in conjunction with the gum-stimulating components of the invention, such a skilled artisan may provide anti-cariogenic and anti-demineralizing agents such as fluoride salts, more particularly sodium monofluorophosphate, sodium fluoride, and stannous fluoride. Depending on the level of fluoride treatment desired, and depending on whether or not a composition is "over-the-counter" or "by prescription", the fluoride will be included in a range from about 0% to about 1% by weight of the dental whitening composition, more preferably in a range from about 0.1% to about 0.5% by weight. Antimicrobial agents, e.g., for fighting gum disease, may be included in conjunction with the gum stimulating components of the invention. Examples of useful antimicrobial agents include chlorohexidine, tetracycline, cetyl pyridinium chloride, benzalkonium chloride, cetyl pyridinium bromide, methyl benzoate, and propyl benzoate. The antimicrobial agents are preferably included in an amount in a range from about 0% to about 15% with the gum stimulating, or in a range from about 1% to about 5% by weight.

One method of dispensing sticky and viscous gum stimulating compositions within the scope of the present invention is by means of a syringe. Squeezable tubes and other similar dispensing devices may also be used to dispense the compositions. Upon dispensing, the gum stimulating compositions are sufficiently viscous that they do not easily settle or spread once dispensed, but will generally remain as a single extruded strand or bead of gum stimulating composition, for example, along the gum line. Moreover, bottles, tubes or other dispensing means known in the art may be used, particularly where the gum stimulating composition has lower viscosity, low stickiness, and does not include a thickening agent.

In some embodiments, the invention provides a unit dose of the gum stimulating compositions in a syringe or similar dispensing device. In this way, the person can load the precise amount of gum stimulating composition onto the dental tray for each treatment period. By using such dispensing devices, the dentist is also able to monitor how many doses the person has received and used. In other embodiments, however, the gum stimulating compositions can be applied directly to the person's teeth without a dental tray, or a less viscous and sticky stimulating composition according to the invention may be used in conjunction with self-retaining trays known in the art.

While a given gum stimulating composition may be able to retain the dental tray against a person's teeth for, e.g., 10 hours or more, that composition could certainly be used within the scope of the present invention for any desired time period, such as for 15 minutes, one hour, or any desired time duration. In order to maximize treatment time and reduce the inconvenience of having a dental tray lodged within a person's mouth the dental trays can be used at night during a person's sleep.

Additional Ingredients

The compositions of the present invention may contain one or more additional skin care or gum care active ingredients.

In general, the additional components should be suitable for application to keratinous tissue, particularly when the composition is to be in contact with human keratinous tissue. Hence, the additional ingredients incorporated into the composition are suitable for contact with human keratinous tissue and do out have undue toxicity, incompatibility, instability, allergic response, and the like within the scope of sound medical judgment.

The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents (clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and panthenol derivatives), aloe vera, pantothenic acid, pantothenic acid derivatives, allantoin, bisabolol, and dipotassium glycyrrhizinate, skin treating agents, thickeners, and vitamins and derivatives thereof.

In any embodiment of the present invention, however, the active ingredients useful herein can be categorized by the benefit they provide or by their postulated mode of action. However, it is to be understood that the active ingredients useful herein can in some instances provide more than one benefit or operate via more than one mode of action. Therefore, classifications herein are made for the sake of convenience and are not intended to limit the active to that particular application or applications listed.

Desquamation Compounds

A safe and effective amount of a desquamation compound may be added to the compositions of the present invention, or from about 0.1% to about 10%, or from about 0.2% to about 5%, or from about 0.5% to about 4%, by weight of the composition. Desquamation compounds enhance the skin appearance benefits of the present invention. For example, the desquamation compounds tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Zwitterionic surfactants such as described in these applications are also useful as desquamatory agents herein, with cetyl betaine being particularly desirable.

Anti-Acne Ingredients

The compositions of the present invention may contain a safe and effective amount of one or more anti-acne active ingredients. Examples of useful anti-acne ingredients include resorcinol, sulfur, benzoyl peroxide, erythromycin, zinc, etc. Further examples of suitable anti-acne compounds are described in further detail in U.S. Pat. No. 5,607,980, issued to McAtee et al, on Mar. 4, 1997.

Anti-Wrinkle Compounds/Anti-Atrophy Compounds

The compositions of the present invention may further contain a safe and effective amount of one or more anti-wrinkle compounds or anti-atrophy compounds. Exemplary anti-wrinkle/anti-atrophy compounds suitable for use in the compositions of the present invention include sulfur-containing D and L amino acids and their derivatives and salts, particularly the N-acetyl derivatives, a preferred example of which is N-acetyl-L-cysteine; thiols (e.g. ethane thiol); phytic acid, lipoic acid; lysophosphatidic acid, skin peel agents (e.g., phenol and the like), vitamin $B_3$ compounds and retinoids that enhance the health and/or appearance of keratinous tissues.

Vitamin $B_3$ Compounds

The compositions of the present invention may contain a safe and effective amount of a vitamin $B_3$ compound. When vitamin $B_3$ compounds are present in the compositions of the instant invention, the compositions can contain from about 0.01% to about 50%, or from about 0.1% to about 10%, or from about 0.5% to about 10%, or from about 1% to about 5%, or from about 2% to about 5%, by weight of the composition, of the vitamin $B_3$ compound.

As used herein, "vitamin $B_3$ compound" means a compound having the formula:

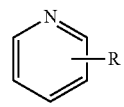

wherein R is —CONH$_2$ (e.g., niacinamide), —COOH (e.g., nicotinic acid) or —CH$_2$OH (e.g., nicotinyl alcohol), derivatives thereof, and salts of any of the foregoing. Exemplary derivatives of the foregoing vitamin B$_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

The vitamin compounds may be included as the substantially pure material, or as an extract obtained by suitable physical and/or chemical isolation from natural (e.g., plant) sources.

Examples of suitable vitamin B$_3$ compounds are well known in the art and are commercially available from a number of sources, e.g., the Sigma Chemical Company (St. Louis, Mo.); ICN Biomedicals, Inc, (Irvin, Calif.) and Aldrich Chemical Company (Milwaukee, Wis.).

Retinoids

The compositions of the present invention may also contain a retinoid. As used herein, "retinoid" includes all natural and/or synthetic analogs of Vitamin A or retinol-like compounds that possess the biological activity of Vitamin A in the skin as well as the geometric isomers and stereoisomers of these compounds. The retinoid can, for example, be retinol, retinol esters (e.g., C$_2$-C$_{22}$ alkyl esters of retinol, including retinyl palmitate, retinyl acetate, retinyl propionate), retinal, and/or retinoic acid (including all-trans retinoic acid and/or 13-cis-retinoic acid). In some embodiments, retinoids other than retinoic acid are used. These compounds are available in the art and are commercially available from a number of sources, e.g., Sigma Chemical Company (St. Louis, Mo.), and Boerhinger Mannheim (Indianapolis, Ind.). Other retinoids that are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. Reissue 34,075, issued Sep. 22, 1992 to Purcell et al. Other suitable retinoids are tocopheryl-retinoate, tocopherol ester of cis- or trans-retinoic acid, adapalene (6-[3-(1-adamantyl)-4-methoxyphenyl]-2-naphthoic acid), and tazarotene (ethyl 6-[2-(4,4-dimethylthiochroman-6-yl)-ethynyl]nicotinate). Desirable retinoids include retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. In some embodiments, the retinoid is substantially pure, or essentially pure.

The compositions of this invention may contain a safe and effective amount of the retinoid, such that the resultant composition is safe and effective for regulating or improving the condition of keratinous tissues. The compositions and methods of the invention can improve visible and/or tactile discontinuities in skin, or improve signs of skin aging. The compositions preferably contain from about 0.005% to about 2%, or from about 0.01% to about 2%, retinoid. Retinol can also be used in an amount of from about 0.01% to about 0.15%. Retinal esters can be used in an amount of from or about 0.01% to or about 2% (e.g., about 1%). Retinoic acids can be used in an amount of from or about 0.01% to about 0.25%. Tocopheryl-retinoate, adapalene, and tazarotene can be used in an amount of from or about 0.01% to or about 2%.

Where the compositions of the present invention contain both a retinoid and a vitamin B$_3$ compound, the retinoid can be used in the above amounts, and the vitamin B$_3$ compound can be used in an amount of from or about 0.1% to about 10%, or from about 2% to about 5%.

Peptides

Peptides, including but not limited to, di-, tri-, tetra-, and pentapeptides and derivatives thereof, may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine (beta-ala-his). Suitable tripeptides for use herein include, gly-his-lys, arg-lys-arg, and his-gly-gly. Preferred tripeptides and derivatives thereof include palmitoyl-gly-his-lys, which may be purchased as Biopeptide CL™ (100 ppm of palmitoyl-gly-his-lys commercially available from Sederma, France); Peptide CK (arg-lys-arg); Peptide CK+ (ac-arg-lys-arg-NH$_2$); and a copper derivative of his-gly-gly sold commercially as Iamin, from Sigma (St. Louis, Mo.). Suitable tetrapeptides for use herein include Peptide E, arg-ser-arg-lys (SEQ ID NO:1). Suitable pentapeptides for use herein include lys-thr-thr-lys-ser (SEQ ID NO:2). A preferred commercially available pentapeptide derivative composition is Matrixyl™, which contains 100 ppm palmitoyl-lys-thr-thr-lys-ser (SEQ ID NO:3, commercially available from Sederma France).

Desirable peptides include palmitoyl-lys-thr-thr-lys-ser, palmitoyl-gly-his-lys, beta-ala-his, their derivatives, and combinations thereof. In some embodiments, the peptide is selected from palmitoyl-lys-thr-thr-lys-ser (SEQ ID NO:3), palmitoyl-gly-his-lys (SEQ ID NO:4), their derivatives, and combinations thereof. In other embodiments, the peptide is selected from palmitoyl-lys-thr-thr-lys-ser (SEQ ID NO:3) and derivatives thereof. When included in the present compositions, peptides can be present in amounts of from about $1\times10^{-6}$% to about 10%, or from about $1\times10^{-6}$% to about 0.1%, or from about $1\times10^{-5}$% to about 0.01%, by weight of the composition. In certain compositions where the peptide is Carnosine™, the compositions can contain from about 0.1% to about 5%, by weight of the composition, of such peptides. In other embodiments wherein the peptide-containing compositions, Matrixyl™, and/or Biopeptide CL™ are included, the compositions can contain from about 0.1% to about 10%, by weight compositions, of Matrixyl™ and/or Biopeptide CL™ peptide-containing compositions.

Anti-Oxidants/Radical Scavengers

The compositions of the present invention may include a safe and effective amount of an anti-oxidant/radical scavenger. The anti-oxidant/radical scavenger is especially useful for providing protection against ultraviolet radiation that can cause increased scaling or texture changes in the stratum corneum and against other environmental agents that can cause skin damage.

A safe and effective amount of an anti-oxidant/radical scavenger may be added to the compositions of the subject invention, for example, from about 0.1% to about 10%, or from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. Other anti-oxidants/radical scavengers are selected from tocopherol sorbate and other esters of tocopherol. For example, the use of tocopherol sorbate in topical compositions and applicable to the present invention is described in U.S. Pat. No. 4,847,071.

Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is useful for providing protection against ultraviolet radiation that can contribute to excessive scaling or skin texture changes and against other environmental agents that can cause skin damage.

A safe and effective amount of a chelating agent may be added to the compositions of the subject invention, for example, from about 0.1% to about 10%, or from about 1% to about 5%, of the composition. Exemplary chelators that are useful herein are disclosed in U.S. Pat. No. 5,487,884; International Publication No. 91/16035, Bush et al., published Oct. 31, 1995; and International Publication No. 91/16034, Bush et al., published Oct. 31, 1995. In some embodiments, the chelators used in compositions of the subject invention include, for example, furildioxime, furilmonoxime, and derivatives thereof.

Flavonoids

The compositions of the present invention may optionally contain a flavonoid compound. Flavonoids are broadly disclosed in U.S. Pat. Nos. 5,686,082 and 5,686,367, both of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, $C_1$-$C_8$ alkyl, $C_1$-$C_4$ alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (e.g. unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',41-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

In some embodiments, unsubstituted flavanone, methoxy flavanones, unsubstituted chalcone, 2',4-dihydroxy chalcone, and mixtures thereof are used in the compositions of the invention. In other embodiments, unsubstituted flavanone, unsubstituted chalcone (especially the trans isomer), and mixtures thereof are used in the compositions of the invention.

Flavonoids can be synthesized or obtained as extracts from natural sources (e.g., plants). The naturally sourced material can also further be derivatized (e.g., an ester or ether derivative prepared following extraction from a natural source). Flavonoid compounds useful herein are also commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.). Mixtures of such flavonoid compounds may also be used.

The flavonoid compounds can be present in the invention, for example, at concentrations of from about 0.01% to about 20%, more preferably from about 0.1% to about 10%, and still more preferably from about 0.5% to about 5%.

Anti-Inflammatory Agents

A safe and effective amount of an anti-inflammatory agent may be added to the compositions of the present invention, for example, from about 0.1% to about 10%, or from about 0.5% to about 5%, of the composition. The anti-inflammatory agent can enhance the appearance of the skin, for example, by contributing to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In some embodiments, the steroidal anti-inflammatory used is hydrocortisone.

A second class of anti-inflammatory agents that is useful in the compositions includes the nonsteroidal anti-inflammatory agents. A variety of compounds are encompassed by this group. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:
1) the oxicams, such as piroxicam, isoxicam, tenoxicam, sudoxicam, and CP-14,304;
2) benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is useful for topical application. Of the nonsteroidal anti-inflammatory agents, ibuprofen, naproxen, flufenamic acid, etofenamate, aspirin, mefenamic acid, meclofenamic acid, piroxicam and felbinac are often used. Ibuprofen, naproxen, ketoprofen, etofenamate, aspirin and flufenamic acid are frequently used.

Moreover, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly Rubia Cordifolia), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, or $C_{10}$-$C_{24}$, or $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Anti-Cellulite Agents

The compositions of the present invention may also contain a safe and effective amount of an anti-cellulite agent. Suitable agents may include, but are not limited to, xanthine compounds (e.g., caffeine, theophylline, theobromine, and aminophylline).

Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tanning Compounds

The compositions of the present invention may contain a tanning compound. When present, the compositions can contain from about 0.1% to about 20%, or from about 2% to about 7%, or from about 3% to about 6%, by weight of the composition, of dihydroxyacetone as an artificial tanning compound.

Dihydroxyacetone, which is also known as DHA or 1,3-dihydroxy-2-propanone, is a white to off-white, crystalline powder. This material can be represented by the chemical formula $C_3H_6O_3$. The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See The Merck Index, Tenth Edition, entry 3167, p. 463 (1983), and "Dihydroxyacetone for Cosmetics", E. Merck Technical Bulletin, 03-304 110, 319 897, 180 588.

Skin Lightening Agents

The compositions of the present invention may contain a skin-lightening agent. When used, the compositions can contain from about 0.1% to about 10%, or from about 0.2% to about 5%, or from about 0.5% to about 2%, by weight of the composition, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the PCT publication No. 95/34280, in the name of Hillebrand, corresponding to PCT Application No. U.S. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication No. 95/23780, published Sep. 8, 1995.

Skin Soothing and Skin Healing Compounds

The compositions of the present invention may comprise a skin soothing or skin-healing compound. Skin soothing or skin healing compounds suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing compound may be added to the present composition, foe example, from about 0.1% to about 30%, or from about 0.5% to about 20%, or from about 0.5% to about 10%, by weight of the composition formed.

Anti-Microbial and Anti-Fungal Compounds

The compositions of the present invention may contain an anti-microbial or anti-fungal compound. Such compounds are capable of destroying microbes, preventing the development of microbes or preventing the pathogenic action of microbes. A safe and effective amount of an anti-microbial or anti-fungal compound may be added to the present compositions, for example, from about 0.001% to about 10%, or from about 0.01% to about 5%, or from about 0.05% to about 2%.

Examples of antimicrobial and antifungal compounds include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Examples of compounds useful herein include those selected from benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Compounds

Exposure to ultraviolet light can result in excessive scaling and texture changes of the stratum corneum. Therefore, the compositions of the subject invention may optionally contain a sunscreen compound. As used herein, "sunscreen compound" includes both sunscreen agents and physical sun blocks. Suitable sunscreen compounds may be organic or inorganic, Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens can be present in the amount of from about 0.1% to about 20%, or from about 0.5% to about 10%, or from about 1% to about 5%, by weight of the composition.

A wide variety of conventional organic sunscreen compounds are suitable for use herein. Sagarin, et al., at Chapter VIII, pages 189 et seq., of Cosmetics Science and Technology (1972), discloses numerous suitable compounds. Specific suitable sunscreen compounds include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates esters (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

Desirable compounds include 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds.

In some embodiments, the organic sunscreen compounds used in the compositions of the invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Useful sunscreen compounds are also described in U.S. Pat. No. 4,937,370 issued to Sabatelli on Jun. 26, 1990, and U.S. Pat. No. 4,999,186 issued to Sabatelli & Spirnak on Mar. 12, 1991. The sun-screening agents disclosed therein have, in a single molecule, two distinct chromophore moieties that exhibit different ultra-violet radiation absorption spectra. One of the chromophore moieties absorbs predominantly in the UVB radiation range and the other absorbs strongly in the UVA radiation range.

Desirable members of this class of sun-screening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N, N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy)

benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof. Other desirable sunscreen compounds include 4,4'-t-butylmethoxydibenzoyl-methane, 2-ethylhexyl-p-methoxycinnamate, phenyl benzimidazole sulfonic acid, and octocrylene.

A safe and effective amount of the organic sunscreen compound is used, typically from about 1% to about 20%, more typically from about 2% to about 10% by weight of the composition. Exact amounts will vary depending upon the sunscreen or sunscreens chosen and the desired Sun Protection Factor (SPF).

Particulate Material

The compositions of the invention may contain a particulate material, for example, a metallic oxide. These particulates can be coated or uncoated, charged or uncharged. Charged particulate materials are disclosed in U.S. Pat. No. 5,997,887, to Ha, et al., incorporated herein by reference. Particulate materials useful herein include; bismuth oxychloride, iron oxide, mica, mica treated with barium sulfate and $TiO_2$, silica, nylon, polyethylene, talc, styrene, polypropylene, ethylene/acrylic acid copolymer, sericite, titanium dioxide, bismuth oxychloride, iron oxide, aluminum oxide, silicone resin, barium sulfate, calcium carbonate, cellulose acetate, polymethyl methacrylate, and mixtures thereof.

Inorganic particulate materials, e.g., $TiO_2$, $ZnO$, or $ZrO_2$ are commercially available from a number of sources. One example of a suitable particulate material contains the material available from U.S. Cosmetics (TRONOX TiO2 series, SAT-T CR837, a rutile $TiO_2$). Particulate materials can be present in the composition in levels of from about 0.01% to about 2%, or from about 0.05% to about 1.5%, or from about 0.1% to about 1%, by weight of the composition.

Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. No. 2,831,854; U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al, issued Apr. 26, 1994; U.S. Pat. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985, Desirable conditioning agents are selected from urea, guanidine, sucrose polyester, panthenol, dexpanthenol, allantoin, and combinations thereof.

Thickening Agent

The compositions of the present invention can contain one or more thickening agents, can be from about 0.1% to about 5%, or from about 0.1% to about 4%, or from about 0.25% to about 3%, by weight of the composition. Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in CTFA International Cosmetic Ingredient Dictionary, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from B.F. Goodrich (e.g., Carbopol™ 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol™ 1342, Carbopol™ 1382, Pemulen TR-1, and Pemulen TR-2, from B.F. Goodrich. In other words, examples of carboxylic acid polymer thickeners useful herein are those selected from carbomers, acrylates/$C_{10}$-$C_{30}$ alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

c) Polyacrylamide Polymers

The compositions of the present invention can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

d) Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. In these polymers, the hydroxy groups of the cellulose polymer is hydroxyalkylated (preferably hydroxyethylated or hydroxypropylated) to form a hydroxyalkylated cellulose that is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the trade name Natrosol™ CS Plus from Aqualon Corporation (Wilmington, Del.).

Other useful polysaccharides include scleroglucans that are a linear chain of (1-3) linked glucose units with a (1-6) linked glucose every three units, a commercially available example of which is Clearogel™ CS11 from Michel Mercier Products Inc. (Mountainside, N.J.).

e) Gums

Other thickening and gelling agents useful herein include materials that are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Compositions of the invention can therefore include desirable thickening agents such as carboxylic acid polymers, crosslinked polyacrylate polymers, polyacrylamide polymers, and mixtures thereof, more preferably selected from carboxylic acid polymers, polyacrylamide polymers, and mixtures thereof.

Composition Preparation

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods for Regulating Skin Condition

The compositions of the present invention are useful for stimulating cellular growth and/or collagen production in keratinous tissues. Such increased cell growth and/or increased collagen production can help regulate or rejuvenate mammalian keratinous tissues. The compositions of the invention can be used for both prophylactic and therapeutic treatment of skin conditions. For example, compositions of the invention can be used for wound healing, thickening keratinous tissue (i.e., building the epidermis and/or dermis layers of the skin and where applicable the keratinous layers of the nail and hair shaft), preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallow-colored mammalian skin, preventing and/or retarding sagging of mammalian skin, softening and/or smoothing lips, hair and nails of a mammal, preventing and/or relieving itch of mammalian skin, regulating skin texture (e.g. wrinkles and fine lines), and improving skin color (e.g. redness, freckles).

Treating keratinous tissues involves topically applying to the keratinous tissue a safe and effective amount of a composition of the present invention. The amount of the composition that is applied, the frequency of application and the period of use will vary widely depending upon the level of the acetylsalicylic acid, gibberellic acid, jasmonic acid, salicylic acid, or zeatin in a given composition and the level of regulation desired, for example, in light of the level of keratinous tissue damage present or expected to occur.

In some embodiments, the composition is chronically applied to the skin. By "chronic topical application" is meant continued topical application of the composition over an extended period during the subject's lifetime, for example, for a period of at least about one week, or for a period of at least about one month, or for at least about three months, or for at least about six months, or for at least about one year. While benefits are obtainable after various periods of use (e.g., five, ten or twenty years), chronic application can continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions that are typically applied per application are, in mg composition/$cm^2$ skin, from about 0.01 mg/$cm^2$ to about 10 mg/$cm^2$. A particularly useful application amount is about 1 mg/$cm^2$ to about 2 mg/$cm^2$.

Regulating keratinous tissue condition can be practiced by applying a composition in the form of a skin lotion, cream, gel, foam, ointment, paste, emulsion, spray, conditioner, tonic, cosmetic, lipstick, foundation, nail polish, after-shave, or the like that is preferably intended to be left on the skin or other keratin structure for some esthetic, prophylactic, therapeutic or other benefit (i.e., a "leave-on" composition). After applying the composition to the skin, it can be left on the skin for a period of at least about 15 minutes, or at least about 30 minutes, or at least about 1 hour, or for at least several hours, for example, up to about 12 hours.

Any part of the external portion of the face, hair, and/or nails can be treated, e.g., face, lips, under-eye area, eyelids, scalp, neck, torso, arms, hands, legs, feet, fingernails, toenails, scalp hair, eyelashes, eyebrows, etc. The composition can be applied with the fingers or with an implement or device (e.g., pad, cotton ball, applicator pen, spray applicator, and the like).

Another approach to ensure a continuous exposure of the skin to at least a minimum level of the beneficial compositions of the invention is to apply the composition in a patch, for example, to selected tissues such as the face. Such an approach is particularly useful for problem skin areas needing more intensive treatment (e.g., a wound, facial crows feet area, frown lines, under eye area, and the like). The patch can be occlusive, semi-occlusive or non-occlusive and can be adhesive or non-adhesive. The composition can be contained within the patch or be applied to the skin prior to application of the patch. The patch can also include additional compounds such as chemical initiators for exothermic reactions such as those described in U.S. Pat. Nos. 5,821,250, 5,981,547, and 5,972,957 to Wu, et al. The patch is preferably left on the skin for a period of at least about 5 minutes, or at least about 15 minutes, or at least about 30 minutes, or at least about 1 hour, or at night as a form of night therapy.

The following examples are intended to further illustrate certain aspects of the invention but are not intended to be limiting thereof.

EXAMPLE 1

Stimulation of Fibroblast Growth

This Example provides data showing the cell proliferating effect of acetylsalicylic acid and salicylic acid on human skin fibroblasts.

Materials and Methods

A human skin fibroblast cell line (Clonetics, Walkersville, Md., normal human dermal fibroblasts, neonatal) was tested to ascertain whether exposure to acetylsalicylic acid and salicylic acid of the invention would stimulate cellular proliferation. The proliferative response of the human skin fibroblast cell line to acetylsalicylic acid and salicylic acid was measured in a 96-well assay system using serum-free medium as a control. Both compounds were tested at three concentrations, $1\times10^{-4}$ M, $1\times10^{-5}$ M and $1\times10^{-6}$ M. Cells ($2\times10^3$) were seeded into a 96 well in 100 µl of Dulbecco's Modified Eagle's Medium (DMEM, Sigma Chemical Co., St. Louis, Mo.) containing 10% fetal bovine serum (FBS, Sigma Chemical Co., St. Louis, Mo.). The plate was incubated for 24 hours at 37° C. in a humidified 5% $CO_2$ atmosphere. After incubation, the medium was aspirated and the wells were rinsed twice with 100 µl of serum-free DMEM. The final rinse was aspirated and 100 µl of the $1\times10^{-4}$M, $1\times10^{-5}$M or $1\times10^{-6}$ M solutions of acetylsalicylic acid and salicylic acid each were added to 5 wells. In addition, 100 µl of vehicle (serum-free DMEM) was added to 5 wells as control. All wells were incubated for 28 hours at 37° C. in a humidified, 5% $CO_2$ atmosphere. After incubation, 20 µl of Cell Titer 96 Aqueous One Solution (Promega, Madison, Wis.) was added to all wells. The plate was swirled gently and placed back in the incubator for 45 minutes and spectrophotometric absorbance was read at 490 nm.

Statistical analyses of data were performed using one-way ANOVA. $P<0.05$ is considered significant, while $P<0.0001$ is considered extremely significant and $P<0.001$ is considered as very significant.

Results

Table 1 and FIG. 1 illustrate the cell proliferating effect of acetylsalicylic acid on human skin fibroblasts, where the concentration of acetylsalicylic acid varied between $1\times10^{-4}$ M (designated ASA4), $1\times10^{-5}$ M (designated ASA5) and $1\times10^{-6}$ M (designated ASA6).

TABLE 1

Effect of Acetylsalicylic acid on Cell Proliferation

| Group | Number of Points | Mean | Standard Deviation | Standard Error of Mean | Median |
|---|---|---|---|---|---|
| Control | 5 | 0.3784 | 0.009317 | 0.004167 | 0.3800 |
| ASA4 | 5 | 0.5406 | 0.03051 | 0.01364 | 0.5290 |
| ASA5 | 5 | 0.6276 | 0.03310 | 0.01480 | 0.6270 |
| ASA6 | 5 | 0.6590 | 0.04973 | 0.02224 | 0.6590 |

The data provided in Table 1 and FIG. 1 indicate that acetylsalicylic acid has strong cell proliferating activity at all concentrations ($P<0.001$ at all concentrations). The effect on cell proliferation was dose dependent, with a greater effect at lower, rather than higher, concentrations.

Figure 2:
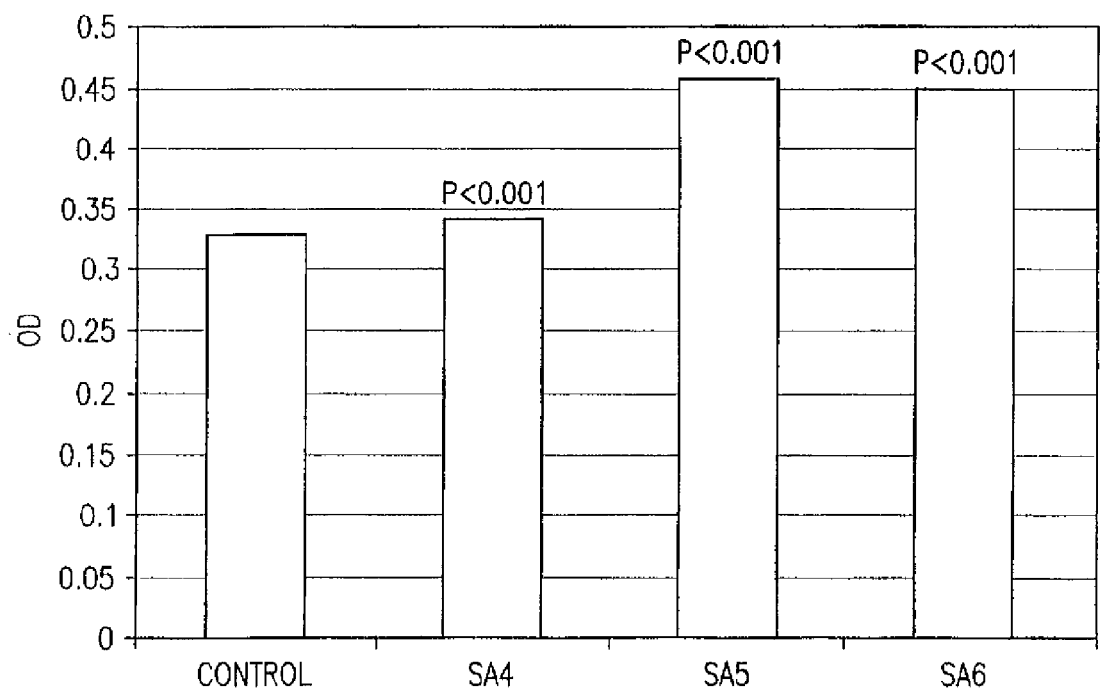
FIG. 2 illustrates the cell proliferating activity of salicylic acid on human skin fibroblasts. The optical density (OD) at 490 nm was used as a measure of cellular density. The concentration of salicylic acid tested varied between $1 \times 10^{-4}$ M (designated SA4), $1 \times 10^{-5}$ M (designated SA5) and $1 \times 10^{-6}$ M (designated SA6). Control cells received no salicylic acid. As illustrated, all concentrations of salicylic acid had a significant effect on cell growth ($P<0.01$ to $P<0.001$), but lower concentrations of salicylic acid ($1 \times 10^{-5}$ M and $1 \times 10^{-6}$ M) had a greater effect ($P<0.001$).

Table 2 and FIG. 2 illustrate the cell proliferating effect of salicylic acid on human skin fibroblasts, where the concentration of salicylic acid varied between $1\times10^{-4}$M (designated SA4), $1\times10^{-5}$ M (designated SA5) and $1\times10^{-6}$ M (designated SA6).

TABLE 2

Effect of Salicylic acid on Cell Proliferation

| Group | Number of Points | Mean | Standard Deviation | Standard Error of Mean | Median |
|---|---|---|---|---|---|
| Control | 5 | 0.3368 | 0.01201 | 0.005370 | 0.3310 |
| SA4 | 5 | 0.3916 | 0.03116 | 0.01393 | 0.4050 |
| SA5 | 5 | 0.5004 | 0.02532 | 0.01133 | 0.5110 |
| SA6 | 5 | 0.4668 | 0.01599 | 0.007151 | 0.4690 |

The data provided in Table 2 and FIG. 2 indicates that salicylic acid has strong cell proliferating activity especially at the lower concentrations ($P<0.001$ at concentrations of $10^{-5}$ and $10^{-6}$M). The effect on cell proliferation was dose dependent mariner with a greater effect at lower, rather than higher, concentrations.

EXAMPLE 2

Stimulation of Keratinocyte Growth

This Example provides data showing the cell proliferating effect of jasmonic acid, zeatin and gibberellic acid on human skin keratinocytes.

Materials and Methods

A human skin keratinocyte cell line from Clonetics (Walkersville, Md., normal human epidermal keratinocytes, neonatal, catalog number cc-2503) was exposed to the jasmonic acid, zeatin and gibberellic acid (from Sigma Chemical Co.) to determine their effect on proliferation of keratinocytes. The proliferative response of these human skin keratinocytes to the test compounds was measured in a 96-well assay system using keratinocyte basal medium (KBM, Clonetics, catalog number CC-3103) as a control. All compounds were tested at three concentrations, $1\times10^{-4}$ M, $1\times10^{-5}$ M and $1\times10^{-6}$ M. Cells were seeded into a 96 well plate at a concentration of $2\times10^3$ cells in 100 µl of KBM. The plate was incubated for 24 hours at 37° C. in a humidified 5% $CO_2$ atmosphere. After incubation, 100 µl of the $1\times10^{-4}$M, $1\times10^{-5}$M or $1\times10^{-6}$ M solutions of jasmonic acid, zeatin and gibberellic acid were added to 5 wells each. In addition, 100 µl of vehicle KBM was added to 5 wells as control. The plate was incubated for 48 hours at 37° C. in a humidified, 5% $CO_2$ atmosphere. After incubation, 20 μl of Cell Titer 96 Aqueous One Solution (Promega, Madison, Wis.) was added to all wells. The plate was swirled gently and placed back in the incubator for 3 hours. The spectrophotometric absorbance of each well was read at 490 nm.

Statistical analyses of data were performed using one-way ANOVA. $P<0.05$ is considered significant, while $P<0.0001$ is considered extremely significant and $P<0.001$ is considered as very, very significant.

Results

Figure 3:
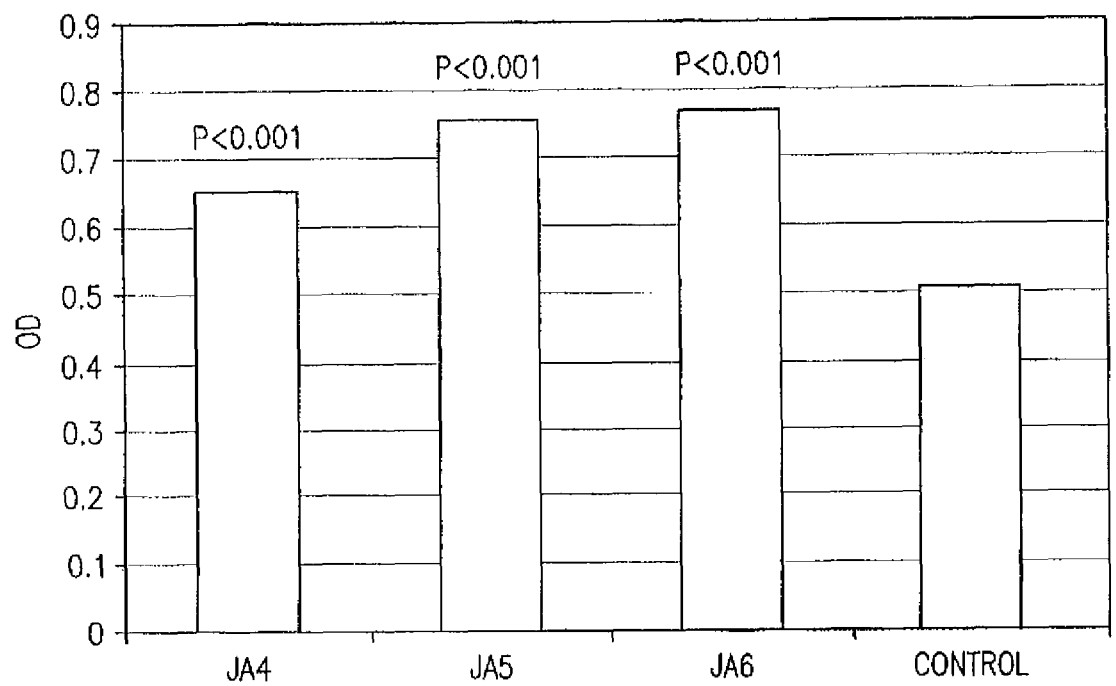
FIG. 3 illustrates the cell proliferating activity of jasmonic acid on human skin fibroblasts. The optical density (OD) at 490 nm was used as a measure of cellular density. The concentration of jasmonic acid tested varied between $1 \times 10^{-4}$ M (designated JA4), $1 \times 10^{-5}$ M (designated JA5) and $1 \times 10^{-6}$ M (designated JA6). Control cells received no jasmonic acid. As illustrated, all concentrations of jasmonic acid had an effect on cell growth ($P<0.05$ to $P<0.001$), but lower concentrations of jasmonic acid ($1 \times 10^{-5}$ M and $1 \times 10^{-6}$ M) had a greater effect ($P<0.001$).

Table 3 and FIG. 3 illustrate the cell proliferating effect of jasmonic acid on human keratinocytes, where the concentration of jasmonic acid varied between $1\times10^{-4}$ M (designated JA4), $1\times10^{-5}$ M (designated JA5) and $1\times10^{-6}$ M (designated JA6).

TABLE 3

Effect of Jasmonic Acid on Cell Proliferation

| Group | Number of Points | Mean | Standard Deviation | Standard Error of Mean | Median |
|---|---|---|---|---|---|
| JA4 | 5 | 0.5732 | 0.02720 | 0.01216 | 0.5860 |
| JA5 | 5 | 0.7628 | 0.03805 | 0.01702 | 0.7750 |
| JA6 | 5 | 0.7734 | 0.06328 | 0.02830 | 0.7970 |
| Control | 5 | 0.5094 | 0.07334 | 0.03280 | 0.5050 |

The data provided in Table 3 and FIG. 3 indicates that jasmonic acid has strong cell proliferating activity especially at the lower concentrations ($P<0.001$ at concentrations of $10^{-5}$ and $10^{-6}$ M). The effect on cell proliferation was greater at lower, rather than higher, concentrations.

Figure 4:
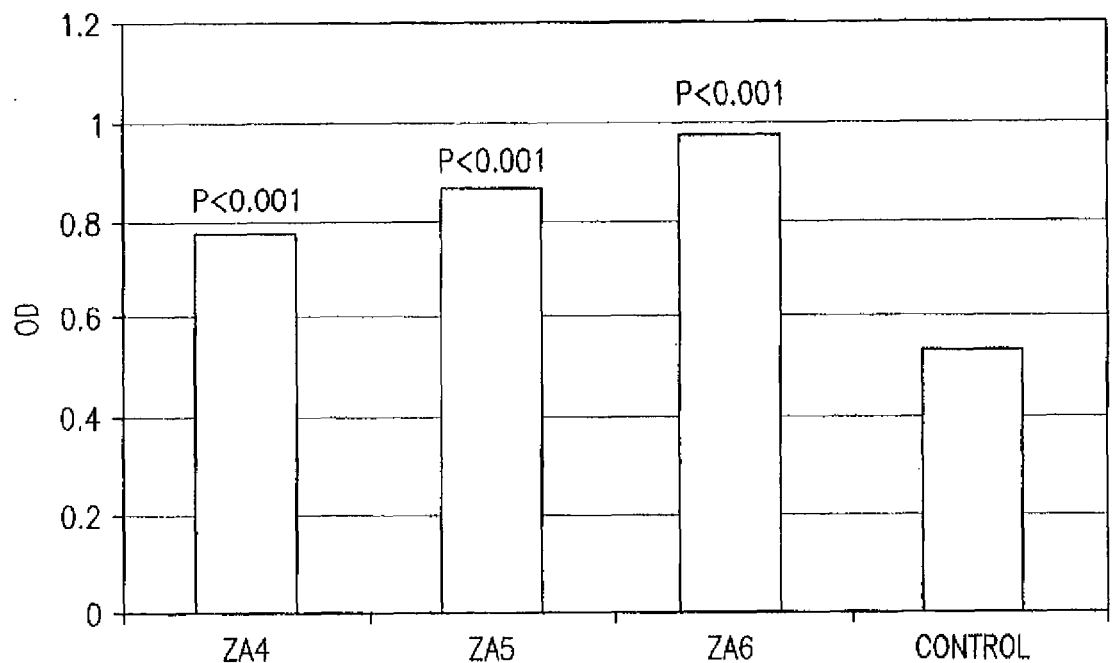
FIG. 4 illustrates the cell proliferating activity of t-zeatin on human skin fibroblasts. The optical density (OD) at 490 nm was used as a measure of cellular density. The concentration of t-zeatin tested varied between $1 \times 10^{-4}$ M (designated ZA4), $1 \times 10^{-5}$ M (designated ZA5) and $1 \times 10^{-6}$ M (designated ZA6). Control cells received no t-zeatin. As illustrated, all concentrations of t-zeatin had a significant effect on cell growth ($P<0.001$). However, the effect of zeatin was dose dependent, with a greater effect observed at lower concentrations.

Table 4 and FIG. 4 illustrate the cell proliferating effect of t-zeatin on human keratinocytes, where the concentration of t-zeatin varied between $1\times10^{-4}$ M (designated ZA4), $1\times10^{-5}$ M (designated ZA5) and $1\times10^{-6}$ M (designated ZA6).

TABLE 4

Effect of t-Zeatin on Cell Proliferation

| Group | Number of Points | Mean | Standard Deviation | Standard Error of Mean | Median |
|---|---|---|---|---|---|
| ZA4 | 5 | 0.7726 | 0.03785 | 0.01693 | 0.7880 |
| ZA5 | 5 | 0.8716 | 0.03179 | 0.01421 | 0.8790 |
| ZA6 | 5 | 0.9770 | 0.05141 | 0.02299 | 0.9830 |
| Control | 5 | 0.5336 | 0.07444 | 0.03329 | 0.5650 |

The data provided in Table 4 and FIG. 4 indicate that t-zeatin has strong cell proliferating activity at all concentrations ($P<0.001$ at all concentrations). The effect on cell proliferation was dose dependent manner with a greater effect at lower, rather than higher, concentrations.

Figure 5:
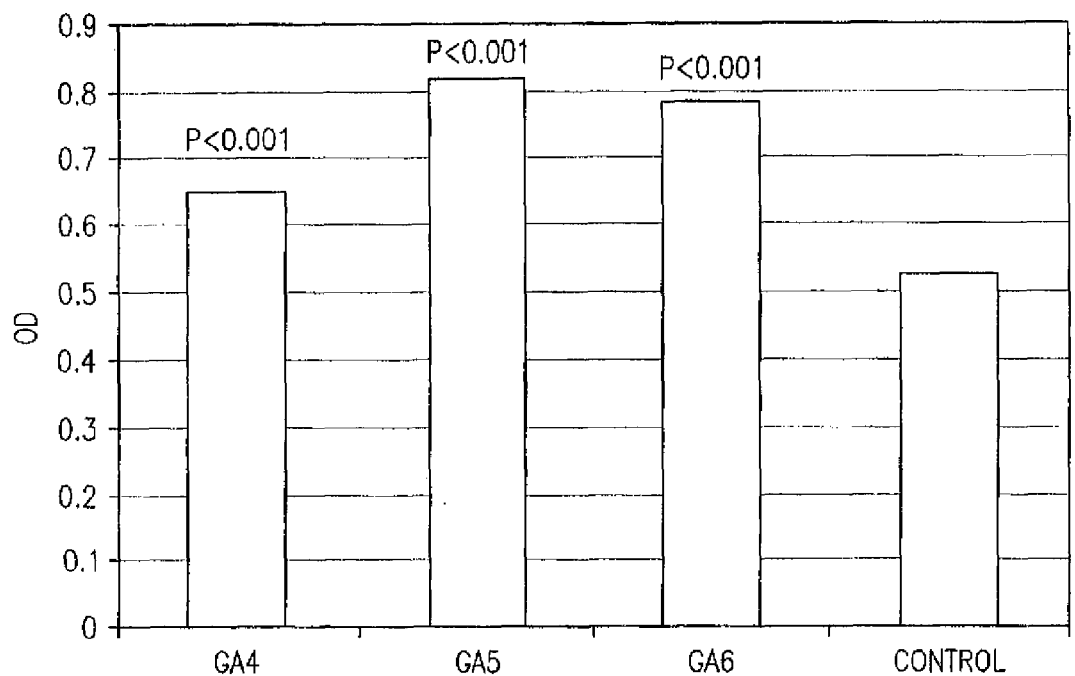
FIG. 5 illustrates the cell proliferating activity of gibberellic acid on human keratinocytes. The optical density (OD) at 490 nm was used as a measure of cellular density. The concentration of gibberellic acid tested varied between $1 \times 10^{-4}$ M (designated GA4), $1 \times 10^{-5}$ M (designated GA5) and $1 \times 10^{-6}$ M (designated GA6). Control cells received no gibberellic acid. As illustrated, all concentrations of gibberellic acid had a significant effect on cell growth ($P<0.001$). However, the effect of gibberellic acid was dose dependent, with a greater effect observed at lower concentrations.

Table 5 and FIG. 5 illustrate the cell proliferating effect of gibberellic acid on human keratinocytes, where the concentration of gibberellic acid varied between $1\times10^{-4}$ M (designated GA4), $1\times10^{-5}$ M (designated GA5) and $1\times10^{-6}$ M (designated GA6).

TABLE 5

Effect of Gibberellic acid on Cell Proliferation

| Group | Number of Points | Mean | Standard Deviation | Standard Error of Mean | Median |
|---|---|---|---|---|---|
| GA4 | 5 | 0.6512 | 0.01256 | 0.005616 | 0.6510 |
| GA5 | 5 | 0.8184 | 0.04813 | 0.02152 | 0.8210 |
| GA6 | 5 | 0.7854 | 0.04743 | 0.02121 | 0.7900 |
| Control | 5 | 0.5308 | 0.06833 | 0.03056 | 0.5220 |

The data provided in Table 5 and FIG. 5 indicate that gibberellic acid has strong cell proliferating activity at all concentrations ($P<0.001$ at all concentrations). The effect on cell proliferation was greater at lower, rather than higher, concentrations.

EXAMPLE 3

Stimulation of Collagen Production

The example provides data showing the effect of jasmonic acid, zeatin and gibberellic acid on collagen production.

The stimulation response of jasmonic acid, zeatin and gibberellic acid on collagen production in the human skin fibroblast cell line (Clonetics, Walkersville, Md., normal human dermal fibroblasts, neonatal, catalog number CC-2509) was measured using Takara Biomedicals EIA assay kit (TAK MK101) sold by Panvera (Madison, Wis.). The cells were first grown in a 96-well assay system using Dulbecco's Modified Eagle's Medium (DMEM) with 10% fetal bovine serum (FBS) both purchased from Sigma Chemical Co, St. Louis, Mo. Serum-free DMEM was used as a control. All compounds were tested at three concentrations $1\times10^{-4}$ M, $1\times10^{-5}$ M and $1\times10^{-6}$ M. Cells were seeded into a 96 well plate at a concentration of $5\times10^3$ cells in 100 μl of DMEM containing 10% fetal bovine serum (FBS, Sigma Chemical Co., St. Louis, Mo.). Plate was incubated for 24 hours at 37° C. in a humidified 5% $CO_2$ atmosphere. After incubation, the medium was aspirated and the wells were rinsed twice with 100 μl of scrum-free DMEM. The final rinse was aspirated and 100 μl of the $1\times10^{-4}$ M, $1\times10^{-5}$ M or $1\times10^{-6}$ M solutions of the test compounds were added to the wells (n=2 for each concentration). In addition, 100 μl of vehicle (scrum-free DMEM) was added to 4 wells as control. The plate was incubated for 48 hours at 37° C. in a humidified, 5% $CO_2$ atmosphere.

The assay was done by using the recommended 20 ul of the supernatant from each well of the 96-well plate. Standard buffer and stop solutions were freshly prepared before running the assay. 100 ul of antibody-POD conjugate solution (supplied with the kit) was added into the wells using pre antibody coated 96 well plate (supplied with the kit). 20 ul of standard and test solutions (from the other 96-well plate containing fibroblasts) were added to appropriate wells. Plate was mixed gently, sealed and incubated for three hrs. at 37° C.

After incubation each well was washed carefully four times with PBS buffer (400 ul). All the wells were completely emptied at the end of washing from any liquid, 100 ul of substrate solution (hydrogen peroxide and tetramethylbenzidine in a buffer solution, supplied with the kit) was added to each well and the plate was incubated for 15 minutes. At this point 100 ul of stop solution (freshly prepared 1N $H_2SO_4$) was added to each well in the same order as substrate. The plate was gently mixed and absorbance was read at 450 nm.

Statistical analyses of data were performed using one-way ANOVA. $P<0.05$ is considered significant, while $P<0.0001$ is considered extremely significant and $P<0.001$ is considered as very, very significant.

Results

Figure 6:
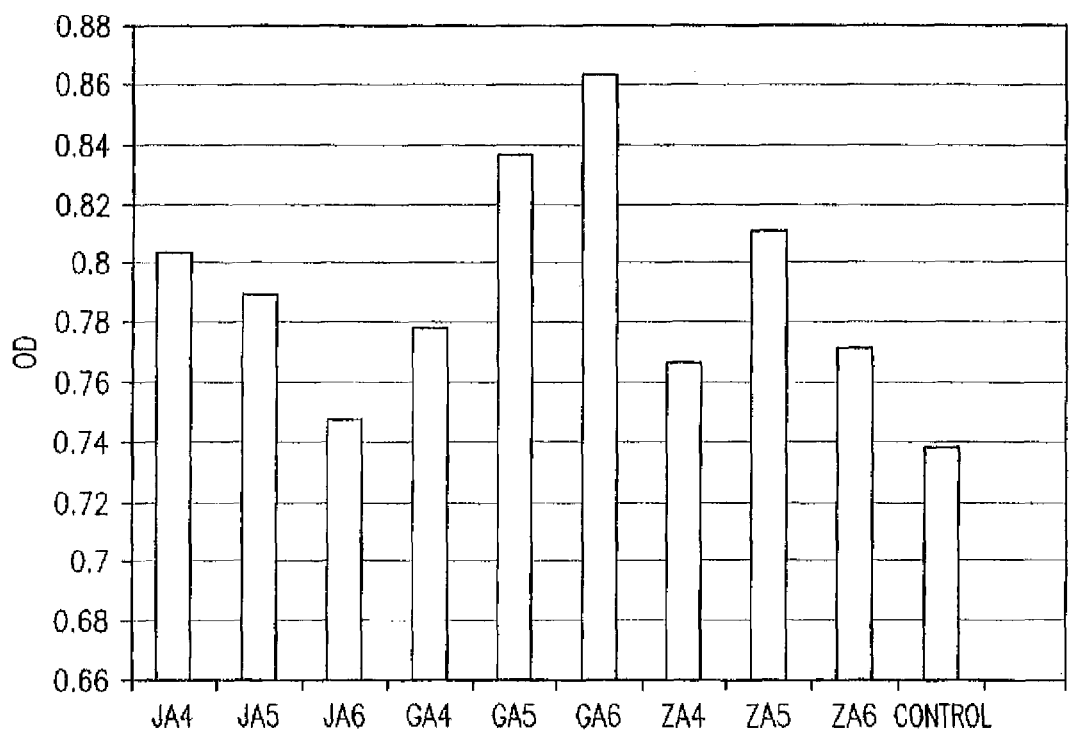
FIG. 6 illustrates the effect of jasmonic acid (JA), gibberellic acid (GA) and zeatin (ZA) on collagen production by human fibroblast cells. The optical density (OD) at 450 nm was used as an indicator of collagen production. The concentration of compound tested varied between $1 \times 10^{-4}$ M (designated 4), $1 \times 10^{-5}$ M (designated 5) and $1 \times 10^{-6}$ M (designated 6). Control cells received no jasmonic acid, gibberellic acid or zeatin. As illustrated, all compounds stimulated collagen production but lower concentrations of gibberellic acid had the most profound effect. Higher concentrations of jasmonic acid and medium concentrations of zeatin also stimulated collagen production.

Table 6 and FIG. 6 illustrate the collagen production of human fibroblast cells exposed to varying concentrations of jasmonic acid, gibberellic acid or t-zeatin. The concentration of jasmonic acid varied between $1\times10^{-4}$ M (designated JA4), $1\times10^{-5}$ M (designated JA5) and $1\times10^{-6}$ M (designated JA6). The concentration of gibberellic acid varied between $1\times10^{-4}$ M (designated GA4), $1\times10^{-5}$ M (designated GA5) and $1\times10^{-6}$ M (designated GA6). The concentration of zeatin varied between $1\times10^{-4}$ M (designated ZA4), $1\times10^{-5}$ M (designated ZA5) and $1\times10^{-6}$ M (designated ZA6).

TABLE 6

Effect of Jasmonic Acid, Gibberellic Acid and Zeatin on Collagen Production by Human Fibroblasts

| Group | Number of Points | Mean | Standard Deviation | Standard Error of Mean | Median |
| --- | --- | --- | --- | --- | --- |
| JA4 | 2 | 0.8040 | 0.009899 | 0.007000 | 0.8040 |
| JA5 | 2 | 0.7895 | 0.006364 | 0.004500 | 0.7895 |
| JA6 | 2 | 0.7475 | 0.007778 | 0.005500 | 0.7475 |
| GA4 | 2 | 0.7780 | 0.01838 | 0.01300 | 0.7780 |
| GA5 | 2 | 0.8365 | 0.04172 | 0.02950 | 0.8365 |
| GA6 | 2 | 0.8630 | 0.008485 | 0.006000 | 0.8630 |
| ZA4 | 2 | 0.7665 | 0.02758 | 0.01950 | 0.7665 |
| ZA5 | 2 | 0.8115 | 0.0007071 | 0.0005000 | 0.8115 |
| ZA6 | 2 | 0.7715 | 0.006364 | 0.004500 | 0.7715 |
| CNA5 | 4 | 0.7483 | 0.006238 | 0.003119 | 0.7495 |
| Control | 4 | 0.7388 | 0.01431 | 0.007157 | 0.7330 |

The data provided in Table 6 and FIG. 6 indicate that jasmonic acid, gibberellic acid and zeatin can all stimulate collagen production in human fibroblasts. The effect of gibberellic acid on collagen production was more profound, particularly at lower, rather than higher, concentrations. However, jasmonic acid strongly stimulated collagen production at higher concentrations and zeatin strongly stimulated collagen production at medium concentrations (see FIG. 6).

All publications and patents are incorporated by reference herein, as though individually incorporated by reference. The invention is not limited to the exact details shown and described, for it should be understood that many variations and modifications may be made while remaining within the spirit and scope of the invention defined by the statements.

---

What is claimed:

1. A method for stimulating collagen production in mammalian fibroblasts in a mammal, the method comprising contacting a plurality of mammalian cells covering an area with a composition comprising a jasmonic acid compound, the plurality of mammalian cells comprising fibroblasts that contact the jasmonic acid compound, wherein contact between the jasmonic acid compound and the fibroblasts stimulates production of collagen by the fibroblasts, wherein the jasmonic acid compound is present at an in situ concentration ranging from about $10^{-6}$ M to about $10^{-4}$ M.

2. The method of claim 1, wherein the composition is applied in a quantity of from about 0.01 milligrams per cubic centimeter of the area.

3. The method of claim 1, wherein the jasmonic acid compound is jasmonic acid.

4. The method of claim 1, wherein the composition further comprises a desquamation compound.

5. The method of claim 4, wherein the desquamation compound includes a sulfhydryl compound, a zwitterionic surfactant, or a mixture thereof.

6. The method of claim 1, wherein the composition is located on a patch, and wherein the method further comprises applying the patch to the plurality of mammalian cells.

7. The method of claim 1, wherein the composition further comprises a gibberellic acid compound, a zeatin compound, or a combination thereof.

8. A method for stimulating collagen production in mammalian fibroblasts in a mammal, the method comprising applying a patch to the epidermis of keratinous tissue, the epidermis overlaying a dermis that contains fibroblasts, wherein the patch comprises a composition including a jasmonic acid compound and an absorbent, wherein the jasmonic acid compound is present at an in situ concentration ranging from about $10^{-6}$ M to about $10^{-4}$ M; and leaving the patch on the epidermis of the keratinous tissue for a period of time, wherein contact between the jasmonic acid compound and the fibroblasts stimulates production of collagen by the fibroblasts.

9. The method of claim 8, wherein the jasmonic acid compound is jasmonic acid.

10. The method of claim 8, wherein the composition further includes a desquamation compound.

11. The method of claim 10, wherein the desquamation compound includes a sulfhydryl compound, a zwitterionic surfactant, or a mixture thereof.

12. The method of claim 8, wherein the composition further comprises a di-, tri-, tetra- or penta-peptide, flavonoid, or a mixture thereof.

13. A method for treating a wound in a mammal, the method comprising applying a composition to a wound in keratinous tissue, the wound being in tissue, the wound tissue comprising fibroblasts, wherein the composition comprises a jasmonic acid compound, and contact between the jasmonic acid compound and the fibroblasts stimulates production of collagen by the fibroblasts, wherein the jasmonic acid compound is present at an in situ concentration ranging from about $10^{-6}$ M to about $10^{-4}$ M.

14. The method of claim 13, wherein the jasmonic acid compound is jasmonic acid.

15. The method of claim 13, the wound covers an area, wherein the composition is applied in a quantity of from about 0.01 milligrams composition per cubic centimeter of the wound area.

16. The method of claim 13, wherein the composition is located on a patch, and wherein the method further comprises applying the patch to the wound area.

17. The method of claim 13, wherein the composition further comprises a gibberellic acid compound, a zeatin compound, or a combination thereof.

* * * * *

```
SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: A synthesized tetrapeptide

<400> SEQUENCE: 1

Arg Ser Arg Lys
1

<210> SEQ ID NO 2
<211> LENGTH: 5
<212> TYPE: PRT
<213> ORGANISM: Artificial Sequence
<220> FEATURE:
<223> OTHER INFORMATION: A synthesized pentapeptide

<400> SEQUENCE: 2

Lys Thr Thr Lys Ser
1               5

<210> SEQ ID NO 3
<211> LENGTH: 5
<212> TYPE: PRT
<213> ORGANISM: Artificial Sequence
<220> FEATURE:
<223> OTHER INFORMATION: A synthesized pentapeptide derivative having
      the sequence palmitoyl-Lys-Thr-Thr-Lys-Ser

<400> SEQUENCE: 3

Lys Thr Thr Lys Ser
1
```